United States Patent [19]

Urrutia

[11] Patent Number: 5,776,109
[45] Date of Patent: Jul. 7, 1998

[54] DRIP CHAMBER FOR INTRAVENOUS FLUID DELIVERY SYSTEM

[76] Inventor: Hector Urrutia, 2404 W. Augusta Sq., McAllen, Tex. 78503

[21] Appl. No.: 701,874

[22] Filed: Aug. 23, 1996

[51] Int. Cl.$^6$ ............................................. A61M 5/00
[52] U.S. Cl. ........................... 604/251; 604/30; 604/403; 604/405
[58] Field of Search ................... 604/7, 27, 30, 604/122, 123, 246, 251, 252, 255, 322, 325, 403, 406, 407; 128/760, 763, 765, 766

[56] References Cited

U.S. PATENT DOCUMENTS

| | | |
|---|---|---|
| 2,762,532 | 9/1956 | Packwood, Jr. . |
| 3,126,125 | 3/1964 | Eggers . |
| 3,490,655 | 1/1970 | Ledgett . |
| 3,664,339 | 5/1972 | Santomieri ............... 604/252 |
| 3,854,637 | 12/1974 | Muller, Jr. et al. . |
| 3,921,630 | 11/1975 | McPhee ................... 604/251 |
| 3,970,490 | 7/1976 | Raines et al. . |
| 4,138,020 | 2/1979 | Steiner et al. . |
| 4,227,525 | 10/1980 | Lundquist ................. 604/252 |
| 4,317,473 | 3/1982 | Gaydos ..................... 604/251 |
| 4,395,260 | 7/1983 | Todd et al. ............... 604/252 |
| 4,548,600 | 10/1985 | Ruschke ................... 604/251 |
| 4,583,979 | 4/1986 | Palti ......................... 604/251 |
| 4,601,414 | 7/1986 | Lawson . |
| 4,601,712 | 7/1986 | Cole et al. ................ 604/251 |
| 4,615,694 | 10/1986 | Raines ...................... 604/406 |
| 4,998,926 | 3/1991 | Alchas ...................... 604/251 |
| 5,489,385 | 2/1996 | Raabe et al. . |
| 5,575,779 | 11/1996 | Barry ........................ 604/255 |

*Primary Examiner*—Mark Bockelman
*Assistant Examiner*—Jennifer R. Sadula
*Attorney, Agent, or Firm*—Oliff & Berridge, PLC

[57] ABSTRACT

A drip chamber for an intravenous fluid delivery system includes a housing having an inlet port and an outlet port, and defining a chamber between the inlet and outlet ports, the housing configured to channel intravenous fluid in a flow path from the inlet port through the chamber and to the outlet port. A member supported in the chamber between the inlet and outlet ports is positioned so that the intravenous fluid flowing through the chamber impinges against the member to reduce the velocity of the intravenous fluid and minimize formation of air bubbles in the intravenous fluid.

25 Claims, 3 Drawing Sheets

DRIP CHAMBER FOR INTRAVENOUS FLUID DELIVERY SYSTEM

BACKGROUND OF INVENTION

1. Field of Invention

This invention generally relates to an intravenous fluid delivery system. More particularly, this invention relates to a drip chamber that minimizes the formation of air bubbles in an intravenous fluid delivery system.

2. Description of Related Art

Intravenous fluid delivery systems are used by medical personnel to provide nutrients and/or medication to a patient via a vein in the patient's arm. Such systems are used during surgery or when a patient is otherwise unable to ingest nutrients or medication orally.

An intravenous fluid delivery system generally includes a bag or container of intravenous fluid that is connected through a series of conduits to a needle inserted into a vein in the patient. The bag or container is supported at a higher elevation than the patient so that intravenous fluid flows through the conduits by the force of gravity.

One or more valves are disposed within the system to control the intravenous fluid flow rate. In addition, a drip chamber is disposed in the conduit arrangement between the intravenous fluid bag and the needle to allow medical personnel to visually inspect the "drip" (i.e., flow rate) of intravenous fluid through the system. From the drip rate, the flow rate of the infused fluid can be calculated. The drip chamber also provides a pocket for the collection of air in the system.

In particular, the drip chamber is constructed of a clear material and has a top inlet port connected to the conduit(s) leading to the intravenous fluid bag and a bottom outlet port connected to the conduit(s) leading to the needle. The inlet and outlet ports enclose opposite ends of a generally-cylindrical column, and fluid drips from the inlet downwardly through the column where it collects at the bottom of the column and exists via the outlet.

When infusing fluids intravenously, particularly under pressurized conditions (such as priming the chamber), the infused fluid flows at a high velocity from the drip chamber inlet opening into a pool of fluid contained in the bottom of the drip chamber. As the high velocity fluid impinges the pool surface, bubbles are entrapped in the fluid pool, thus causing an air-bubble mixture to form. This requires a time-consuming effort to purge the air bubbles from the conduits leading to the patient. If air bubbles are not purged, they may enter the patient and cause an embolism or other harmful effects.

SUMMARY OF INVENTION

Accordingly, the present invention is directed to a drip chamber that substantially obviates one or more of the problems due to limitations and disadvantages of the related art.

To achieve these and other advantages and in accordance with the purpose of the invention, as embodied and broadly described, the invention comprises a housing having an inlet port and an outlet port and defining a chamber between the inlet and outlet ports, whereby intravenous fluid flows from the inlet through the chamber and exits via the outlet. A member supported in the chamber between the inlet and the outlet is positioned so that the intravenous fluid flowing from the inlet and through the chamber impinges against the member to reduce the velocity of the intravenous fluid.

Additional features and advantages of the invention will be set forth in the description which follows, and in part will be apparent from the description, or may be learned by practice of the invention. The objectives and other advantages of the invention will be realized and attained by the apparatus particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention. In the drawings.

DETAILED DESCRIPTION OF THE INVENTION

Reference will now be made in detail to the present preferred embodiments of the invention, examples of which are illustrated in the accompanying drawings.

Figure 1:
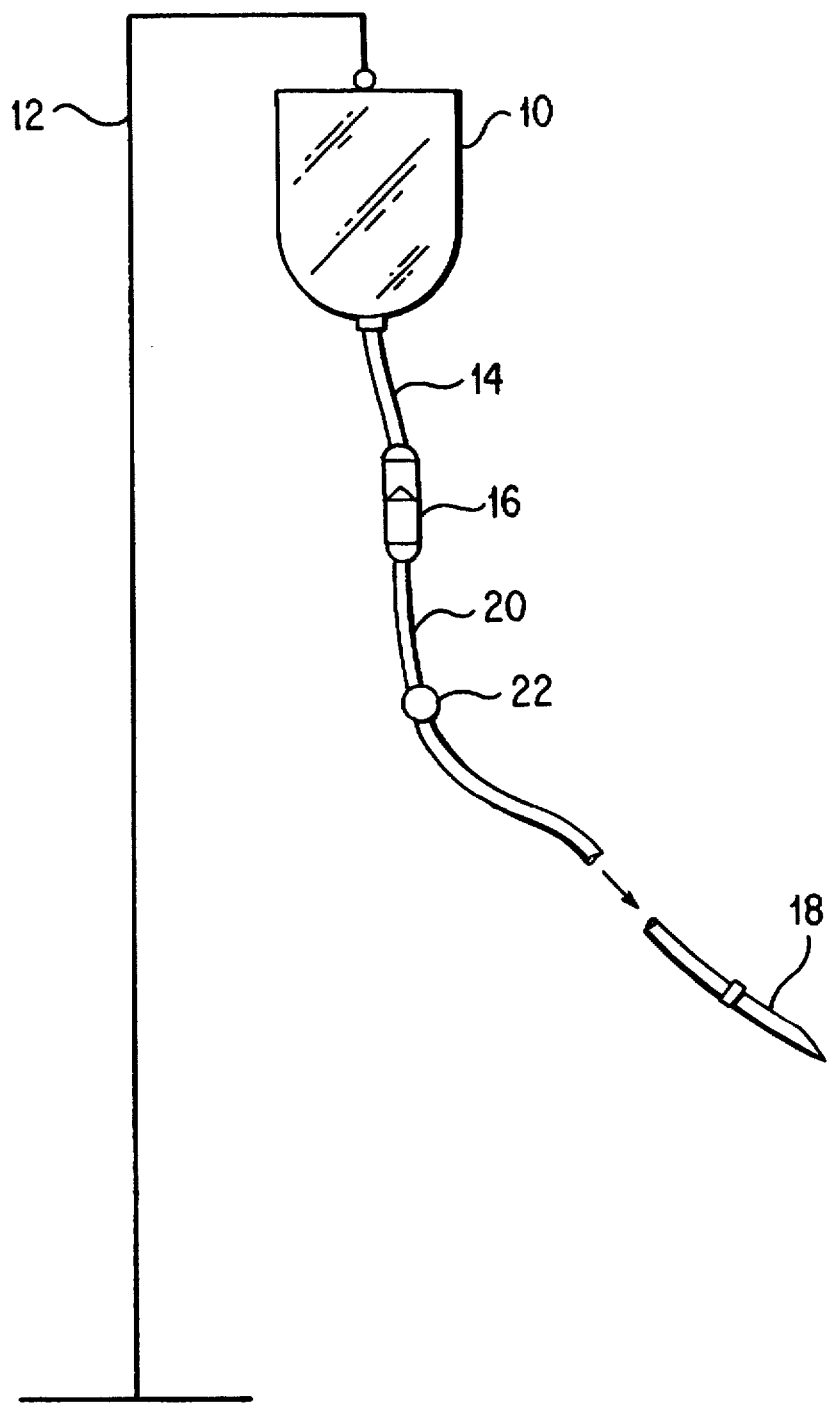
FIG. 1 is a diagram of an intravenous fluid delivery system including a drip chamber of the present invention.

An intravenous fluid delivery system in which the drip chamber of the present invention is used is shown in FIG. 1. The system generally includes an intravenous fluid bag or container 10 supported by a stand 12 at an elevation higher than the patient to effect intravenous infusion by gravitational force. The outlet of container 10 is connected through a conduit 14 to the inlet of a drip chamber 16. The outlet of the drip chamber 16 is connected to a needle 18 through a conduit 20. A valve 22 is located in the conduit 20 between the drip chamber outlet and the needle 18 to control the flow rate of the intravenous fluid. The needle 18 is then inserted into the vein of the patient to complete delivery of the fluid.

Figure 2:
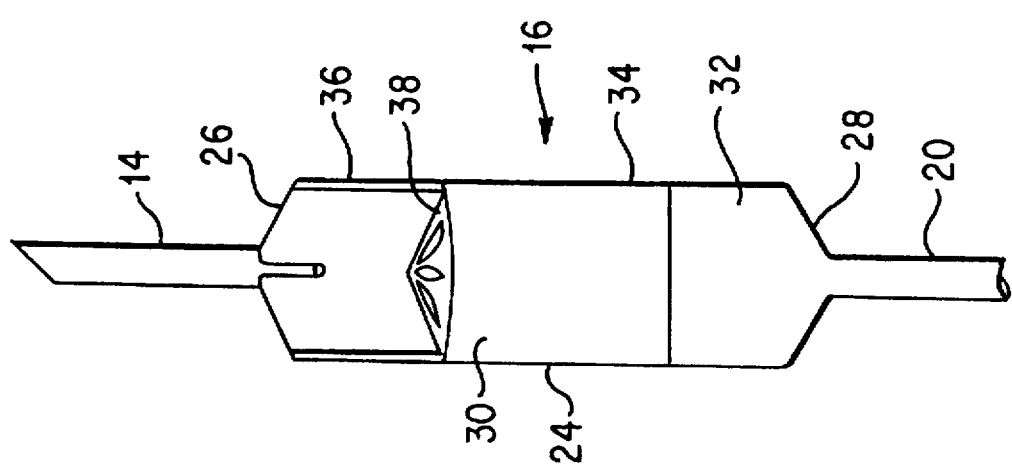
FIG. 2 is an elevation view of a drip chamber of the present invention.

The drip chamber of the present invention is shown in greater detail in FIG. 2. The drip chamber 16 includes a cylindrical housing 24 enclosed at its top end by an inlet port 26 and at its bottom end by an outlet port 28. The inlet port 26 is connected via conduit 14 in flow communication with the intravenous fluid bag 10. Outlet port 28 is connected via conduit 20 in flow communication with needle 18. The housing also defines an internal chamber or column 30 through which intravenous fluid flows, normally in droplet form.

Under normal operating conditions, intravenous fluid from bag 10 enters the drip chamber 16 through inlet port 26 and droplets fall from the inlet port 26 through chamber 30, where they collect in a pool 32 at the bottom of housing and eventually exit via outlet port 28. The rate at which the droplets fall through the chamber represents the flow rate of the system, which is controlled by valve 22. Since the system generally contains no mechanism for tracking the flow rate, the housing is preferably composed of a clear material to allow visual inspection of the "drip" or flow rate of the intravenous fluid through the system. Clear plastic or other suitable materials may be used for the housing.

One of the functions of the drip chamber is to prime the system at the beginning of a procedure or whenever a new bag 10 is added to the system. Priming is necessary to fill the conduits with intravenous solution and purge air from the system. To prime the system, the drip chamber 16 is squeezed manually with valve 22 in the closed position. Release of the drip chamber creates negative pressure in the system and draws intravenous fluid from the bag and through the system. The valve is then opened, whereby a jet of intravenous fluid enters the chamber.

To allow compression of the drip chamber for priming, the housing of the embodiment in FIG. 2 includes a lower portion 34 made of flexible material. An upper portion 36 is preferably rigid and will not flex when lower portion 34 is compressed. Alternatively, the entire housing may be made flexible.

The high-velocity jet of intravenous fluid entering the drip chamber during priming tends to form air bubbles in the intravenous fluid pool 32 in the bottom of the housing. Air bubbles may also form under normal operating conditions as droplets impinge the pool 32. To reduce entrapment of air bubbles in the pool, the drip chamber includes a member or obstacle 38 positioned in the chamber 30 and supported by side walls of the housing 24. The member is positioned directly in the intravenous fluid flow path below the inlet port 26 so that the fluid impinges against the member, thereby decreasing the flow velocity (and kinetic energy) of the fluid prior to its impingement on the surface of the pool 32 in the drip chamber. The fluid then passes through the member and falls into the pool 32, at a lower velocity. Lowering the velocity of the fluid minimizes the formation of air bubbles in the pool.

The member 38 is placed in the housing 24 perpendicular to the intravenous fluid flow. As shown in FIG. 2, the member 38 is positioned in the rigid upper chamber 36 or at the boundary between the upper and lower portions. As a result, the member may be made of any suitable rigid material. Alternatively, if the member is positioned in flexible lower portion 34, or if the entire chamber is made flexible, the member 38 must also be made flexible to permit compression of the housing and must also be resilient and thus capable of returning to its original shape.

Figure 3:
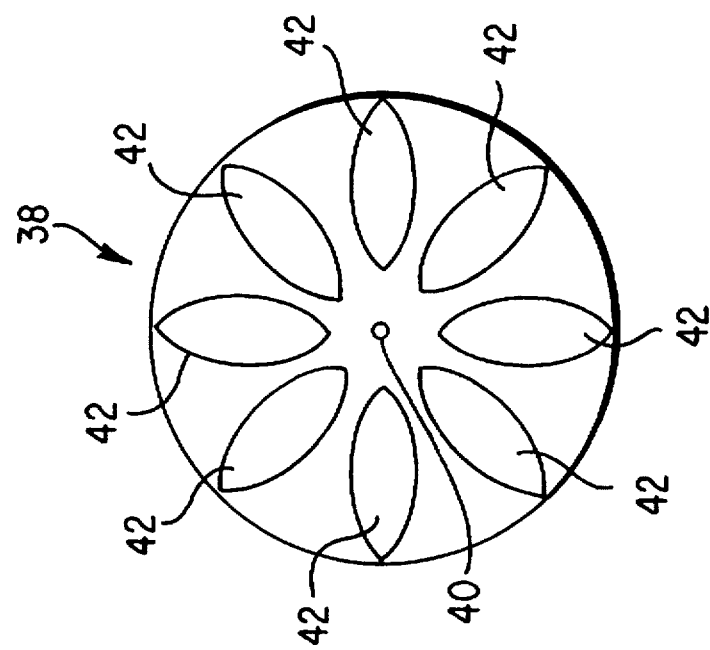
FIG. 3 is an end view of the drip chamber shown in FIG. 2.

Because the purpose of the member 38 is to decrease the flow velocity of the intravenous fluid, any member that impedes fluid flow should sufficiently meet this objective. As shown in FIGS. 2 and 3, one embodiment of the member 38 is conically shaped with an apex 40 facing inlet port 26. Slots 42 are formed in the member 38 to allow the fluid to pass through the member and into the pool. The number and shape of the slots 42 are variable, so long as the slots allow sufficient passage of fluid through the member.

Figure 5:
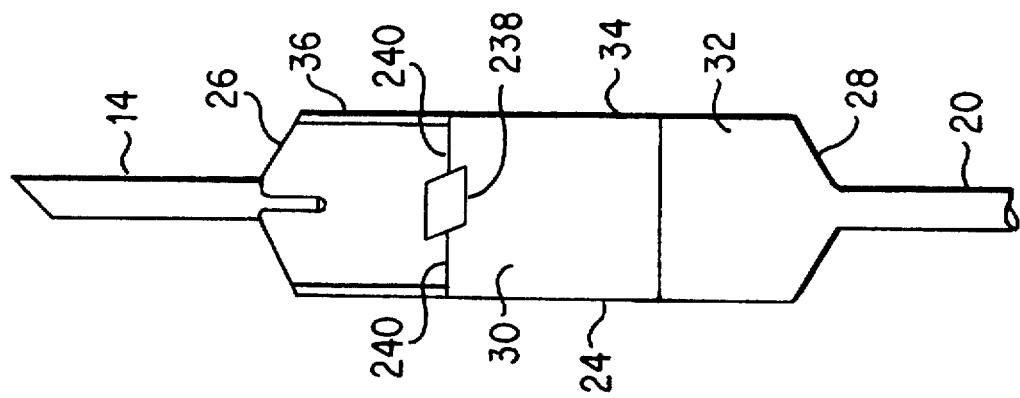
FIG. 5 is an elevation view of another alternative embodiment of the drip chamber of the present invention.
Figure 4:
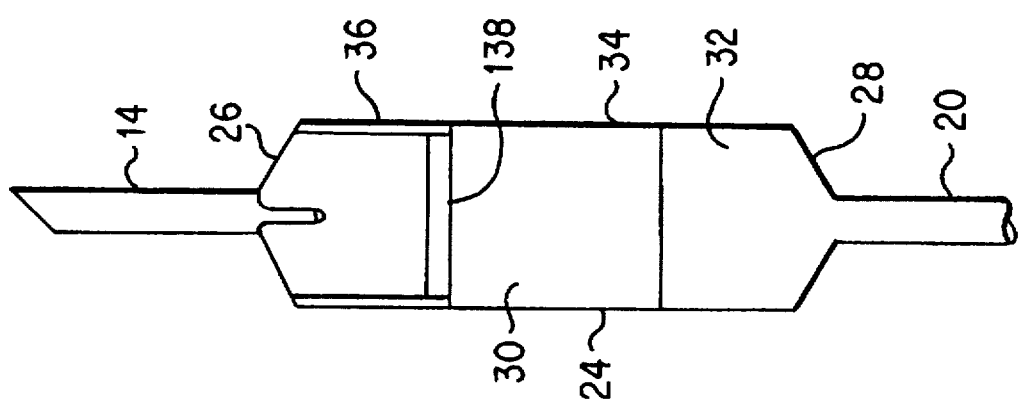
FIG. 4 is an elevation view of an alternative embodiment of the drip chamber of the present invention.

In another embodiment shown in FIG. 4, member 138 may include a rectangular or cylindrical bar that extends from one wall of the housing to the opposite wall, with at least a portion of the bar positioned in the fluid flow path to obstruct fluid flow. In another embodiment shown in FIG. 5, the member includes an inclined plate 238 attached to the housing wall with arms 240. The angle of inclination is not critical so long as the plate sufficiently reduces the flow velocity of the fluid. Angles ranging from 45°–90° with respect to the longitudinal axis of the drip chamber are preferable. Various other embodiments, such as triangular- or spherical-shaped members are possible, so long as the member is dimensioned to reduce the velocity of the fluid and permit the fluid to flow through to the bottom of the housing. The member may also direct the fluid against the side walls of the housing, which may further reduce the flow velocity.

It will be apparent to those skilled in the art that various modifications and variations can be made in the drip chamber of the present invention without departing from the spirit or scope of the invention. Thus, it is intended that the present invention cover the modifications and variations of this invention provided they come within the scope of the appended claims and their equivalents.

What is claimed is:

1. A drip chamber for an intravenous fluid delivery system, comprising:

a housing comprising an inlet port and an outlet port, and at least one side wall defining a chamber between the inlet and outlet ports, the housing configured to channel intravenous fluid in a flow path from the inlet port through the chamber to the outlet port; and a member supported by the at least one side wall in the chamber between, and spaced from both, the inlet and outlet ports and positioned so that the intravenous fluid flowing into the chamber impinges against the member to reduce the velocity of the intravenous fluid and minimize formation of air bubbles in the intravenous fluid, the intravenous fluid impinging against the member flowing directly from the member to the outlet port.

2. The drip chamber of claim 1, wherein the housing includes first and second portions, the second portion being substantially flexible to permit compression of the housing.

3. The drip chamber of claim 2, wherein the first portion is substantially rigid.

4. The drip chamber of claim 2, wherein the member is positioned in the first portion of the housing.

5. The drip chamber of claim 2, wherein the member is positioned at the boundary between the first and second housing portions.

6. The drip chamber of claim 1, wherein the housing is substantially flexible to permit compression of the housing.

7. The drip chamber of claim 1, wherein the member is substantially rigid.

8. The drip chamber of claim 1, wherein the member is substantially flexible.

9. The drip chamber of claim 1, wherein the member is conically shaped with an apex facing the inlet port, the member having slots therein to permit the flow of intravenous fluid through the member.

10. The drip chamber of claim 1, wherein the member comprises a plate extending in a direction substantially perpendicular to the flow path.

11. The drip chamber of claim 1, wherein the member comprises a bar extending from opposite sides of the housing and in a direction substantially perpendicular to the flow path.

12. An intravenous fluid delivery system, comprising:

an intravenous fluid container;

a drip chamber including a cylindrical housing comprising an upper inlet port at one end of the housing and in flow communication with the intravenous fluid container and a lower outlet port at an opposite end of the housing, the housing further comprising at least one side wall defining a chamber between the inlet and outlet ports, and configured to channel intravenous fluid in a flow path from the inlet port through the chamber to the outlet port, and a member supported by the at least one side wall in the chamber between, and spaced from both, the inlet and outlet ports and positioned in the flow path to disperse the intravenous fluid flowing from the inlet and thereby reduce the velocity of the intravenous fluid flowing toward the outlet port, the intravenous fluid impinging against the member flowing directly from the member to the outlet port; and means, in flow communication with the outlet port of the drip chamber, for delivering the intravenous fluid to a patient.

13. The system of claim 12, wherein the housing includes upper and lower portions, the lower portion being substantially flexible to permit compression of the housing walls.

14. The system of claim 13, wherein the upper portion is substantially rigid.

15. The system of claim 13, wherein the member is positioned in the upper portion of the housing.

16. The system of claim 13, wherein the member is positioned at the boundary between the upper and lower portions.

17. The system of claim 12, wherein the housing is substantially flexible to permit compression of the housing.

18. The system of claim 12, wherein the member is substantially rigid.

19. The system of claim 12, wherein the member is substantially flexible.

20. The system of claim 12, wherein the member is conically shaped with an apex facing toward the inlet port, the member having slots therein to permit the flow of fluid through the member.

21. The system of claim 12, wherein the member comprises a plate extending in a direction substantially perpendicular to the flow path.

22. The system of claim 12, wherein the member comprises a bar extending from opposite sides of the housing and in a direction substantially perpendicular to the flow path.

23. The system of claim 12, wherein the member is configured to direct the intravenous fluid against a side wall of the housing.

24. A drip chamber for an intravenous fluid delivery system, comprising:

a housing comprising an inlet port and an outlet port, and at least one side wall defining a chamber between the inlet and outlet ports, the housing configured to channel intravenous fluid in a flow path from the inlet port trough the chamber to the outlet port; and a bar supported at least one end by the at least one side wall in the chamber and spaced from both the inlet and outlet ports so that the intravenous fluid flowing into the chamber impinges against the member to reduce the velocity of the intravenous fluid and minimize formation of air bubbles in the intravenous fluid.

25. A drip chamber for an intravenous fluid delivery system, comprising:

a housing having an inlet port and an outlet port, and defining a chamber between the inlet and outlet ports, the housing configured to channel intravenous fluid in a flow path from the inlet port through the chamber to the outlet port; and a conically-shaped member supported in the chamber between the inlet and outlet ports and having an apex facing the inlet port, the member positioned so that the intravenous fluid flowing into the chamber impinges against the member to reduce the velocity of the intravenous fluid and minimize formation of air bubbles in the intravenous fluid, the member comprising slots extending radially from a position proximate the apex toward a periphery of the member to permit fluid to pass through the member after impingement.

* * * * *